| United States Patent [19]
Erhardt et al. | [11] Patent Number: 4,743,612
[45] Date of Patent: May 10, 1988 |

[54] PRODRUG DERIVATIVES OF THE CARDIOTONIC AGENT 4-ETHYL-1,3-DIHYDRO-5-(4-(2-METHYL-1H-IMIDAZOL-1-YL)BENZOYL)-2H-IMIDAZOL-2-ONE, COMPOSITION CONTAINING THEM, AND METHOD OF USING THEM TO TREAT CARDIAC FAILURE

[75] Inventors: Paul W. Erhardt, Long Valley; Alfred A. Hagedorn, III, Edison, both of N.J.

[73] Assignee: Berlex Laboratories, Inc., Cedar Knolls, N.J.

[21] Appl. No.: 920,086

[22] Filed: Oct. 17, 1986

[51] Int. Cl.[4] .............. A61K 31/415; C07D 233/70; C07D 401/14

[52] U.S. Cl. ..................................... 514/392; 548/318

[58] Field of Search ......................... 548/318; 514/392

[56] References Cited

U.S. PATENT DOCUMENTS 4,552,880 11/1985 Dage et al. ........................... 548/318
4,556,665 12/1985 Erhardt et al. ...................... 548/318

Primary Examiner—Henry R. Jiles
Assistant Examiner—Kurt G. Briscoe
Attorney, Agent, or Firm—Elizabeth A. Bellamy; John L. White; I. William Millen

[57] ABSTRACT

Orally active prodrug derivatives of the cardiotonic agent 4-ethyl-1,3-dihydro-5-[4-(2-methyl-1H-imidazol-1-yl)benzoyl]-2H-imidazol-2-one are disclosed. Pharmaceutical formulations containing such compounds are also provided.

31 Claims, 2 Drawing Sheets

PRODRUG DERIVATIVES OF THE CARDIOTONIC AGENT 4-ETHYL-1,3-DIHYDRO-5-(4-(2-METHYL-1H-IMIDAZOL-1-YL)BENZOYL)-2H-IMIDAZOL-2-ONE, COMPOSITION CONTAINING THEM, AND METHOD OF USING THEM TO TREAT CARDIAC FAILURE

BACKGROUND OF THE INVENTION

The present invention relates to novel mono and dicarbonyl derivatives of the compound 4-ethyl-1,3-dihydro-5-[4-(2-methyl-1H-imidazol-1-yl)benzoyl]-2H-imidazol-2-one. This compound and its use as a cardiotonic agent are disclosed in U.S. Pat. No. 4,556,665, issued Dec. 3, 1985 to Paul W. Erhardt, et al. The compound is unique in that its cardiovascular profile is that of a selective inotropic agent. This in contradistinction to its analog the compound 4-ethyl-1,3-dihydro-5-[4-(1H-imidazol-1-yl)benzoyl]-2H-imidazol-2-one wherein the methyl group on the imidazole ring is missing. This latter compound whilst a potent cardiotonic agent also displays pronounced vascular effects.

In addition to a major biological differentiation between these 2 compounds a still greater difference occurs as to oral bioavailability. The latter compound, 4-ethyl-1,3-dihydro-5-[4-(1H-imidazol-1-yl)benzoyl]-2H-imidazolyl-2-one, that is the compound without the methyl group on the imidazole ring, is nearly 100% bioavailable on oral dosing. The pure inotrope 4-ethyl-1,3-dihydro-5-[4-(2-methyl-1H-imidazol-1-yl)benzoyl]-2H-imidazol-2-one on the other hand is at best 20% bioavailable on oral dosing. The object of this invention is to derivatize this compound in such a manner as to make it, via oral dosing, at least bioavailable.

GENERAL DESCRIPTION OF THE INVENTION COMPOSITION OF MATTER ASPECT

In its composition-of-matter aspect this invention relates to novel mono and dicarbonyl derivatives of the cardiotonic agent 4-ethyl-1,3-dihydro-5-[4-(2-methyl-1H-imidazol-1-yl)benzoyl]-2H-imidazol-2-one and the pharmaceutically acceptable acid addition salts thereof.

Particularly, this invention relates to the novel compounds defined by the following Formula I.

wherein
R is H or $R_1$ is phenyl or a $C_1$–$C_5$ straight or branched chain alkyl group optionally substituted by a hydroxy or phenyl group; or a pharmaceutically acceptable acid addition salt thereof. As used herein the term $C_1$–$C_5$ straight or branched chain alkyl represents for example methyl, ethyl, propyl, isopropyl, butyl, tert-butyl, pentyl and isopentyl. The term $C_1$–$C_5$ straight or branched chain alkyl optionally substituted by a hydroxy or phenyl group can be defined non-exclusively as hydroxymethyl, hydroxyethyl, hydroxypropyl, benzyl, phenylethyl or phenylpropyl.

Among the compounds as defined in Formula I are sites for possible steroisomerism, e.g. asymmetric carbon atoms. Any of the optical isomers thus possible are considered to be part of this invention, as are mixtures of such optical isomers in any proportions.

Also contemplated as part of this invention are the pharmaceutically acceptable acid addition salts of the compounds of Formula I. These acid addition salts may be formed with inorganic or organic acids. Illustrative but not limiting examples of such acids include hydrochloric, hydrobromic, sulfuric, phosphoric, acetic, benzoic, methanesulfonic, and 2-hydroxyethanesulfonic acid. In comparison to the parent compounds these salts usually exhibit greater solubility in water and hydrophilic organic solvents.

Preferred classes of compounds embodied by this invention are those in the above Formula I wherein R is defined as and wherein $R_1$ is defined as a phenyl or $C_1$–$C_5$ straight or branched chain alkyl group, more particularly $C_1$–$C_3$ straight or branched chain alkyl group.

The most preferred classes of compounds embodied by this invention are those in the above Formula I wherein R is defined as hydrogen and $R_1$ is defined as phenyl or $C_1$–$C_5$ straight or branched chain alkyl group, more particularly $C_1$–$C_3$ straight or branched chain alkyl group.

The compounds which follow are some of those which serve to exemplify the various composition-of-matter aspects of the invention decribed herein.

1. 1,3-Dibenzoyl-4-ethyl-1,3-dihydro-5-[4-(2-methyl-1H-imidazol-1-yl)benzoyl]-2H-imidazol-2-one.
2. 1,3-Diacetyl-4-ethyl-1,3-dihydro-5-[4-(2-methyl-1H-imidazol-1-yl)benzoyl]-2H-imidazol-2-one.
3. 4-Ethyl-1,3-dihydro-5-[4-(2-methyl-1H-imidazol-1-yl)benzoyl]-1,3-bis[2-methyl-1-oxopropyl]-2H-imidazol-2-one.
4. 4-Ethyl-1,3-bis[2-ethyl-1-oxobutyl]-1,3-dihydro-5-[4-(2-methyl-1H-imidazol-1-yl)benzoyl]-2H-imidazol-2-one.
5. 4-Ethyl-1,3-dihydro-5-[4-(2-methyl-1H-imidazol-1-yl)benzoyl]-1,3-bis[1-oxohexyl]-2H-imidazol-2-one.
6. 4-Ethyl-1,3-dihydro-5-[4-(2-methyl-1H-imidazol-1-yl)benzoyl]-1,3-bis[1-oxo-2-phenylethyl]-2H-imidazol-2-one.
7. 4-Ethyl-1,3-dihydro-5-[4-(2-methyl-1H-imidazol-1-yl)benzoyl]-1,3-bis[2-methyl-1-oxo-2-phenylethyl]-2H-imidazol-2-one.
8. 4-Ethyl-1,3-dihydro-1,3-bis[3-hydroxy-1-oxopropyl]-5-[4-(2-methyl-1H-imidazol-1-yl)benzoyl]-2H-imidazol-2-one.
9. 4-Ethyl-1,3-dihydro-1,3-bis[3-hydroxy-1-oxobutyl]-5-[4-(2-methyl-1H-imidazol-1-yl)benzoyl]-2H-imidazol-2-one.
10. 4-Ethyl-1,3-dihydro-1,3-bis[5-hydroxy-1-oxopentyl]-5-[4-(2-methyl-1H-imidazol-1-yl)benzoyl]-2H-imidazol-i2-one.
11. 1-Benzoyl-4-ethyl-1,3-dihydro-5-[4-(2-methyl-1H-imidazol-1-yl)benzoyl]-2H-imidazol-2-one.

12. 1-Acetyl-4-ethyl-1,3-dihydro-5-[4-(2-methyl-1H-imidazol-1-yl)benzoyl]-2H-imidazol-2-one.

13. 4-Ethyl-1,3-dihydro-5-[4-(2-methyl-1H-imidazol-1-yl)benzoyl]-1-(2-methyl-1-oxopropyl)-2H-imidazol-2-one.

14. 4-Ethyl-1-[2-ethyl-1-oxobutyl]-1,3-dihydro-5-[4-(2-methyl-1H-imidazol-1-yl)benzoyl]-2H-imidazol-2-one.

15. 4-Ethyl-1,3-dihydro-5-[4-(2-methyl-1H-imidazol-1-yl)benzoyl]-1-(1-oxohexyl)-2H-imidazol-2-one.

16. 4-Ethyl-1,3-dihydro-5-[4-(2-methyl-1H-imidazol-1-yl)benzoyl]-1-(1-oxo-2-phenylethyl)-2H-imidazol-2-one.

17. 4-Ethyl-1,3-dihydro-5-[4-(2-methyl-1H-imidazol-1-yl)benzoyl]-1-(2-methyl-1-oxo-2-phenylethyl)-2H-imidazol-2-one.

18. 4-Ethyl-1,3-dihydro-1-[3-hydroxy-1-oxopropyl]-5-[4-(2-methyl-1H-imidazol-1-yl)benzoyl]-2H-imidazol-2-one.

19. 4-Ethyl-1,3-dihydro-1-[3-hydroxy-1-oxobutyl]-5-[4-(2-methyl-1H-imidazol-1-yl)benzoyl]-2H-imidazol-2-one.

20. 4-Ethyl-1,3-dihydro-1-[5-hydroxy-1-oxopentyl]-5-[4-(2-methyl-1H-imidazol-1-yl)benzoyl]-2H-imidazol-2-one.

PROCESS ASPECT

The compounds of this invention can be prepared, in general, by standard techniques analogous to those known in the art. The method of preparing the principal starting material of this invention, 4-ethyl-1,3-dihydro-5-[4-(2-methyl-1H-imidazol-1-yl)benzoyl]-2H-imidazol-2-one, A is described in detail in U.S. Pat. No. 4,556,665 issued to Paul W. Erhardt et al. on Dec. 3, 1985, which is herein incorporated by reference.

Suggested procedures for the preparation of the compounds of this invention are described below.

The compounds II and III of the foregoing scheme wherein R and R₁ are as previously defined being acyl derivatives of A, may be prepared from A by various procedures for acylation on nitrogen known in the art. Suitable acylating reagents are, for example, the acid halides (that is, the acid chlorides, acid bromides and acid fluorides) corresponding to the acyl moiety to be introduced. Other suitable reagents are the symmetrical anhydrides containing the acyl moiety to be introduced. An additional substituent, which itself would be reactive to acylating agents, but which is desired in the final acyl group, may be protected by a suitable protecting group, or may be masked in the form of another functional group which can subsequently be transformed into the desired substituent. For example, a hydroxyl group in the desired acyl moiety may be protected as its benzyl or tertiary butyl ether in the acylation reaction, and the desired hydroxyl group may be liberated by hydrogenolysis or treatment with acidic reagents, respectively. Alternatively, hydroxyl functions may be stored in nonreactive form as carbonyl groups, that is, as aldehydes or ketones, which groups may then be converted into the desired hydroxyl group by reduction with, for example, sodium borohydride or catalytic hydrogenation. The reaction may be carried out by combining A with about one molar equivalent to about 100 molar equivalents of the acylating reagent, alone or in the presence of a suitable non-reactive solvent, at a temperature from about 25° C. to about 200° C., depending on the reactivity of the acylating reagent and the boiling point of the solvent, if used. The reaction is allowed to proceed for about one hour to about 100 hours, depending on the reactivity of the acylating agent, the proportions of A and acylating agent, and the concentrations of A and acylating agent in the solvent, if one is used. The progress of the reaction may be followed by thin-layer chromatography, high performance liquid chromatography, nuclear magnetic resonance spectrometry or any other suitable analytical method, whereby the consumption of A and/or the formation of II and III may be monitored. The products II and III may be isolated by standard procedures known in the art, for example, removal of solvent and excess acylating reagent by distillation and/or sublimation, followed by purification of the product or products by such methods as extraction with various solvents, crystallization and chromatography.

The products II and III may also be prepared by the reaction of metallic derivatives of A with acylating agents such as those described above. Suitable metallic derivatives are the alkali metal derivatives of A, such as the lithium, sodium and potassium derivatives; the alkaline earth derivatives such as the magnesium and calcium derivatives; and substituted ammonium derivatives such as the tetramethylammonium and tetraethylammonium derivatives or other tetraalkyl- or tetraarylammonium derivatives. These derivatives may be obtained by the reaction of A with about one molar equivalent of a basic salt of the desired metal or ammonium cation, such as the metal or ammonium hydroxide, metal or ammonium alkoxide, metal hydride, metal amide, and the like. This reaction, which is the reaction of the chosen base with the acidic protons on the imidazolone nitrogen atoms of A may be conducted in such solvents as water, alcohols, ethers, dimethylsulfoxide, amides such as N,N-dimethylformamide and N-methylpyrrolidinone, and the like, the solvent being chosen so as not to react irreversibly with the chosen base. The metal or ammonium derivative may crystallize from the reaction mixture, or may be precipitated from the reaction mixture by the addition of an inert solvent, or may be isolated by evaporation of the solvent from the reaction mixture. If desired, the derivative may be purified by crystallization from a suitable solvent. The reaction of these derivatives of A with the chosen acylating agent is conducted in the same fashion as described for A itself, except that lower reaction temperatures and smaller excesses of acylating agent usually may be employed. The derivatives II and III are isolated and purified employing the same methods already outlined.

In general, both II and III may be prepared employing similar reaction conditions. The relative proportions of these two products may be controlled by suitable changes in the reaction conditions, depending on which of the two derivatives is desired. Usually, the monoacyl derivative II can be made to predominate by employing shorter reaction times, smaller excesses of acylating agent, and lower reaction temperatures; the diacyl derivative III can be made to predominate by employing longer reaction times, greater excesses of acylating reagent, and higher temperatures. By the correct choice of purification methods, each of the products may be obtained in a high state of purity.

When the monoacyl derivative II is the desired product, it can be obtained from the diacyl product III or from mixtures of II and III by controlled removal of the second acyl group present in III. This conversion may be achieved by reaction of III (or of mixtures containing III) by treatment with mildly nucleophilic reagents such as water, lower alcohols, alkylamines such as triethylamine, dilute aqueous or alcoholic solutions of alkaline reagents such as sodium hydroxide, sodium bicarbonate and ammonia, and the like. The reaction temperature, reaction time and concentration of alkaline reagent, if used, are adjusted to give maximum conversion of III to the desired II while minimizing the further deacylation of II to A. In general, the diacyl compounds III are more reactive towards nucleophiles than are the monoacyl compounds II, permitting efficient formation of the latter compounds. The conversion of III to II, whether starting with pure III or with mixtures of III and II, may be monitored by standard analytical methods such as thin-layer chromatography, high performance liquid chromatography, and nuclear magnetic resonance spectrometry. The desired products II may then be isolated and purified by procedures such as crystallization and chromatography which are known in the art.

METHOD OF USE AND PHARMACEUTICAL COMPOSITION ASPECT

The object of this invention is to develop an orally effective, selective inotropic agent to be used in the treatment of congestive heart failure. The term selective inotropic agent refers to the ability of a compound to produce an in vivo positive inotropic response (an increase in the rate of left ventricular pressure development; dP/dt), without producing a significant increase in heart rate nor a decrease in mean arterial blood pressure.

U.S. Pat. No. 4,556,665 issued Dec. 3, 1985 to Paul W. Erhardt, et al. discloses and claims certain imidazole-aroyl-imidazolones as inotropic agents. Whilst all of the compounds display inotropic activity there are three agents of special importance: 4-Ethyl-1,3-dihydro-5-[4-(1H-imidazol-1-yl)benzoyl]-2H-imidazol-2-one (Compound A); 4-Ethyl-1,3-dihydro-5-[4-[2-methyl-1H-imidazol-1-yl)benzoyl]-2H-imidazol-2-one (Compound B); and 4-Ethyl-1,3-dihydro-5-[4-(2-ethyl-1H-imidazol-1-yl)benzoyl]-2H-imidazole-2-one (Compound C) which are illustrated below.

Compound A Y = H
Compound B Y = CH₃
Compound C Y = CH₂CH₃

In this homologous series of compounds, only one, Compound B, has a selective inotropic profile. The intravenous administration of Compound B to pentobarbital anesthetized dogs produces little or no effect on mean arterial blood pressure (<5% decrease) nor heart rate (<5% increase) at a dose which produces a 50% increase in left ventricular dP/dt. At a dose of Compound B which produces a 100% increase in left ventricular dP/dt, changes in mean arterial blood pressure and heart rate are in the range of 10%. In contrast, the intravenous administration of either Compound A or Compound C produces a decrease (>10%) in blood pressure and an increase in heart rate (>10%) under conditions where left ventricular dP/dt is increased by 50%. These two compounds produced even greater effects on heart rate and blood pressure at doses which induce a 100% increase in left ventricular dP/dt. These data indicate that the methyl substitution in the 2 position of the imidazole ring of this structural series confers a unique and desirable biological response: inotropic selectivity.

However, surprisingly in another aspect Compound B is an anomaly in this homologous group. When Compounds A, B and C are administered orally or intraduodenally to dogs, the activity of Compound B is greatly diminished, whereas Compounds A and C continue to display their particular activities. It was found that this low activity was due to the fact that whereas Compounds A and C are nearly 100% bioavailable, Compound B is only about 15–20% bioavailable. Further, the dose dependency for Compound B ceases after the first dose, that is, there is no additional pharmacological effect for Compound B when a second oral or intraduodenal dose is given within 90 minutes of the previous dose.

Thus, there was a need to provide a prodrug form of Compound B which would exhibit the selective inotropic effect of Compound B via oral dosing. The prodrug approach envisions that an initial derivatized form of Compound B, after its absorption from the GI tract, is converted to Compound B in the plasma by a hydrolytic and/or enzymatic cleavage process. Substituents such as:

where R″ represents alkyl, aryl, aralkyl, or peptidyl of one to six amino acid units, when appropriately bonded to one or more hetero atoms in the parent molecule such as oxygen or nitrogen can be contemplated as potential prodrug derivatives. Using such technology, with this invention the specific compounds of Formula I provide just such a solution to the need. The compounds of Formula I, especially as exemplified by 1-benzoyl-4-ethyl-1,3-dihydro-5-[4-(2-methyl-1H-imidazol-1-yl)benzoyl]-2H-imidazol-2-one (Compound D), impart such oral bioavailability to Compound B. For instance, Compound D is at least 75% bioavailable and is very consistent in producing selective inotropic responses when given by the oral route.

BRIEF DESCRIPTION OF THE DRAWINGS

Illustrative of the inability of Compound B to produce significant increases in left ventricular dP/dt (less than 15% increase) when given orally to conscious dogs (a solution 3 mg/kg given by oral gavage) is the attached FIG. 1.

Contrasted to this is the aformentioned Compound A of the homology where oral doses of this compound from 3 to 300 µg/kg produce dose dependent increases in left ventricular dP/dt (up to 100% increase noted with 300 µg/kg) as illustrated in the attached FIG. 2. As heretofore mentioned the goal of this invention was to produce a prodrug of Compound B whereby Compound B is orally available as a selective inotropic agent. Best illustrative of this intended goal is Compound D of the attached FIG. 3, wherein it can be seen that at one-third the dose of Compound B, Compound D produces a prolonged and up to 60% increase in left ventricular dP/dt.

METHOD OF USE AND PHARMACEUTICAL COMPOSITION ASPECT CONTINUED

Figure 1:
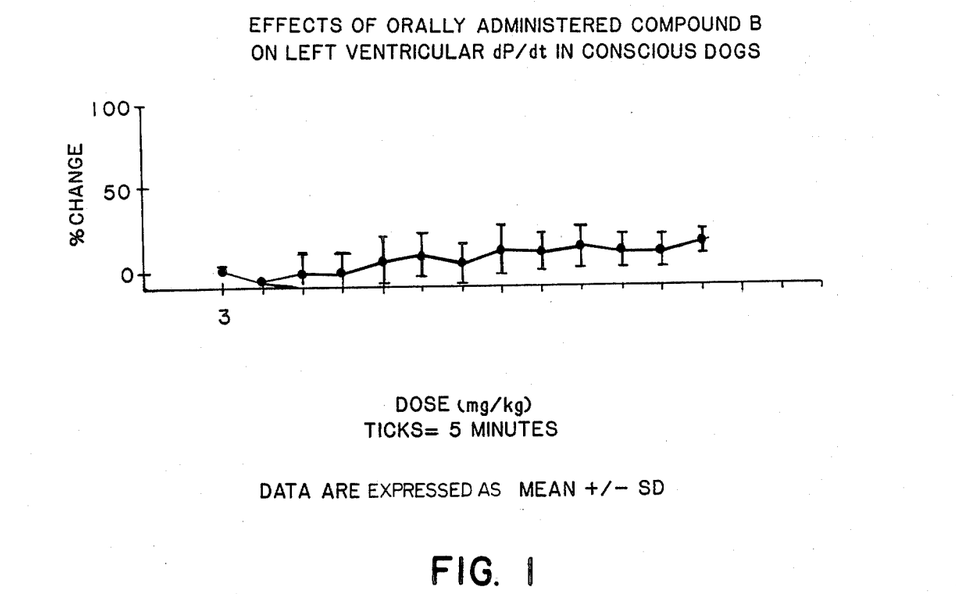
Figure 2:
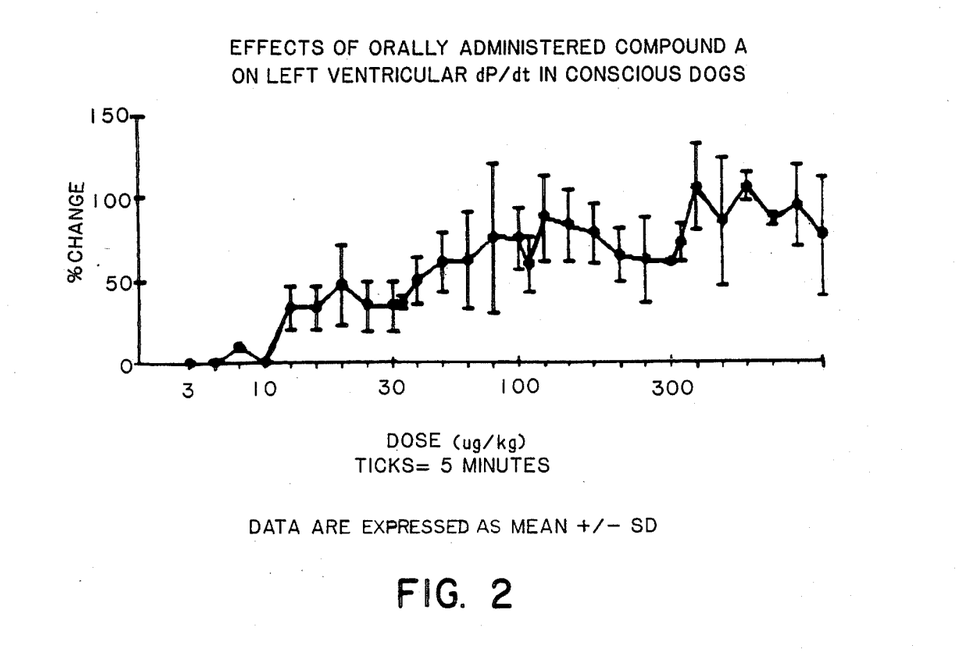
Figure 3:
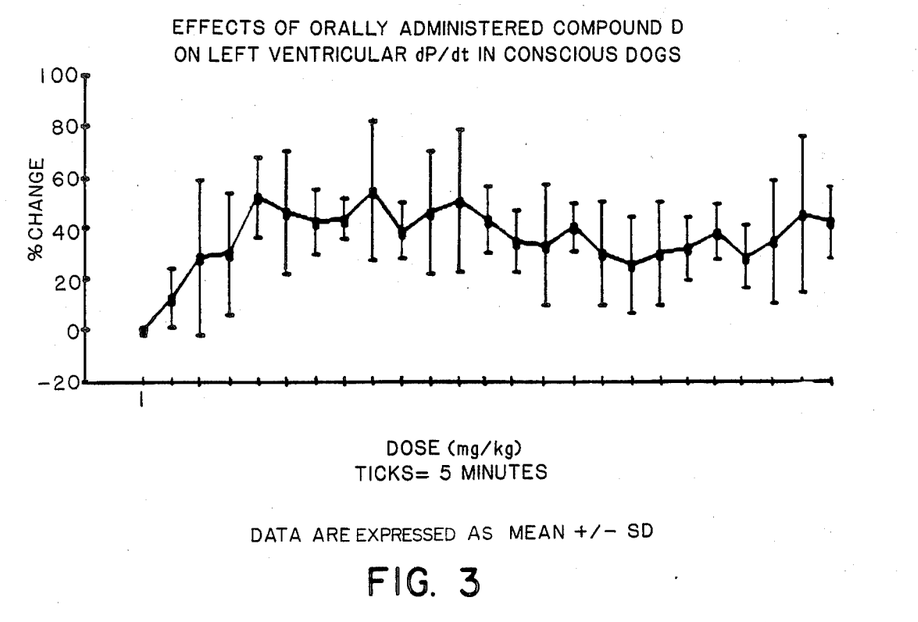

The compounds of Formula I are designed primarily but not exclusively for oral use. The route and dose administered will be dependent on the mammalian host being treated and the magnitude and type of cardiotonic effect to be elicited.

For oral administration the effective cardiotonic dose of the compounds of this invention, for example, 1-benzoyl-4-ethyl-1,3-dihydro-5-[4-(2-methyl-1H-imidazol-1-yl)-benzoyl]- 2H-imidazol-2-one (Compound D), ranges from about 0.001 mg/kg of body weight to about 30 mg/kg of body weight. Repetitive dosing may be required to achieve the appropriate positive inotropic effect for 24 hours.

The orally administratable formulations can be solid or liquid preparations such as capsules, pills, tablets, troches, lozenges, melts, powders, solutions, suspensions or emulsions. The solid unit dosage forms can be a capsule of the ordinary gelatin type containing the compound or an enteric coated compound admixed with dessicants, buffers, surfactants, lubricants such as stearic acid or magnesium stearate and inert fillers such as lactose, sucrose and cornstarch in combination with binders, such as acacia, cornstarch or gelatin, and disintegrating agents such as potato starch or alginic acid.

Whilst the compounds of this invention are primarily for oral administration they may also be administered parenterally. Such parenteral administration, for instance, via intramuscular or intravenous routes, can be accomplished with any number of pharmaceutically acceptable carriers and diluents to constitute an injectable liquid solution. Commonly used diluents and carriers include water or saline solutions, and buffered aqueous solutions including dispensing and surface active agents if necessary.

Thus, there is provided by this invention a method for orally treating cardiac failure in a mammalian host having a chronic condition in which therapeutic benefit is derived from elicitation of a cardiotonic effect which comprises orally administering to said host a non-toxic cardiotonically effective amount of a compound of Formula I in admixture with a non-toxic pharmaceutically acceptable carrier.

The invention described herein above is illustrated below in the Examples, which, however, are not to be construed as limiting the scope of this invention.

EXAMPLES

EXAMPLE I

4-Ethyl-1,3-dihydro-5-[4-(2-methyl-1H-imidazol-1-yl)benzoyl]-2H-imidazol-2-one Sodium Salt.

To 5 g (0.017 mol) of 4-ethyl-1,3-dihydro-5-[4-(2-methyl-1H-imidazol-1-yl)benzoyl]-2H-imidazol-2-one and 0.92 g (0.017 mol) sodium methoxide is added 250 mL methanol. The suspension is stirred overnight at room temperature under nitrogen. The solvent is removed via distillation at 70° C. under nitrogen and the residue is dried in vacuo to provide the title compound.

EXAMPLE II (1)

1,3-Dibenzoyl-4-ethyl-1,3-dihydro-5-[4-(2-methyl-1H-imidazol-1-yl)benzoyl]-2H-imidazol-2-one.

and (2)

1-Benzoyl-4-ethyl-1,3-dihydro-5-[4-(2-methyl-1H-imidazol-1-yl)benzoyl]2H-imidazol-2-one.

To a mixture of 4 g (0.013 mol) of the product of Example I in 30 mL of N,N-dimethylformamide is added in one portion a solution of 4.3 g (0.019 mol) benzoic anhydride in 25 mL of N,N-dimethylformamide. The reaction mixture is heated under nitrogen at 60° C. overnight. The reaction mixture is filtered and the solvent is removed by Kugelrohr distillation in vacuo ($\leq 55°$ C.). The residue is chromatographed on a silica gel column using methylene chloride/methanol 96:4 to provide the subject compounds.

Compd. (1) $R_f=0.69$ (silica gel-acetonitrile:water 9:1)
NMR (DMSO-$d_6$): $\delta=1.07(t,3)$, 2.23(s,3), 2.72 (q,2), 6.92(s,1), 7.35(s,1), 7.45(t,2), 7.54–7.60(m,5), 7.70(t,1), 7.86(d,2), 8.08(d,2) and 8.16(d,2) ppm.

Compd. (2) $R_f=0.53$ (silica gel-acetonitrile:water 9:1)
NMR (DMSO-$d_6$): $\delta=1.13(t,3)$, 2.24(s,3), 2.36(q,2), 6.92(d,1), 7.34(d,1), 7.51(m,4), 7.63(t,1), 7.85(d,2), 7.91(d,2) and 11.52(br s,1) ppm.

EXAMPLE III 1,3-Diacetyl-4-ethyl-1,3-dihydro-5-[4-(2-methyl-1H-imidazol-1-yl)benzoyl]-2H-imidazol-2-one.

A combination of 6 g (0.02 mol) of 4-ethyl-1,3-dihydro-5-[4-(2-methyl-1H-imidazol-1-yl)benzoyl]-2H-imidazol-2-one, 204 mL of acetic anhydride and 5.0 g (0.05mol) of triethylamine is heated at 80°–90° C. for 5 hours. The solvent is removed by Kugelrohr distillation and the resultant oil crystallized from anhydrous ether to afford the title compound.

NMR (DMSO-$d_6$): $\delta=1.05(t,3)$, 1.91(s,3), 2.35(s,3), 2.46(s,3), 2.59–2.64(q+s,5), 6.95(d,1), 7.41(d,1), 7.59(d,2) and 7.98(d,2) ppm.

EXAMPLE IV

1-Acetyl-4-ethyl-1,3-dihydro-5-[4-(2-methyl-1H-imidazol-1-yl)benzoyl]-2H-imidazol-2-one.

Method A. A combination of 6 g (0.02 mol) of 4-ethyl-1,3-dihydro-5-[4-(2-methyl-1H-imidazol-1-yl)benzoyl]-2H-imidazol-2-one, 103 g (1.01 mol) of acetic anhydride and 5.05 g (0.05 mol) triethylamine is heated with stirring between 85°–90° C. until the reaction mixture becomes homogenous, approximately 3 hours. The solvent is removed by Kugelrohr distillation and the resultant oil crystallized with isopropyl alcohol and hexane. The resultant solid is recrystallized from hot methanol to afford the title compound.

Method B. A combination of 10 g (0.034 mol) of 4-ethyl-1,3-dihydro-5-[4-(2-methyl-1H-imidazol-1-yl)benzoyl]-2H-imidazol-2-one, 172 g (1.69 mol) of acetic anhydride and 8.5 g (0.085 mol) of triethylamine is heated with stirring at 85°–90° C. until the reaction mixture becomes homogeneous (approximately 3 hours). The solvent is removed by rotary evaporation (0.05 torr, 60° C.) and the resultant oil is partitioned between 150 mL 1N HCl and 100 mL ether. The aqueous layer is neutralized with 10% NaHCO$_3$ until the pH is above 7. The aqueous layer is extracted with dichloromethane (150 mL, then 50 mL) and the combined organic extracts are dried with sodium sulfate, filtered, and evaporated to afford a solid which is largely diacylated material.

A combination of this solid, 9.2 g (0.09 mol) of triethylamine and 100 mL of 2-propanol is refluxed with stirring for 5 hours. The solvent is evaporated and the resulting solid is recrystallized from warm methanol to afford the title monoacylated compound.

NMR (DMSO-d$_6$): δ=1.10(t,3), 2.33(m,5) 2.43(s,3) 6.95(s,1), 7.39(s,1), 7.55(d,2), 7.85(d,2) and 11.40(br s, 1) ppm.

EXAMPLE V

4-Ethyl-1,3-dihydro-5-[4-(2-methyl-1H-imidazol-1-yl)-benzoyl]-1-(2-methyl-1-oxopropyl)-2H-imidazol-2-one.

To a mixture of 5.0 g (15.7 mmol) of the product of Example I in 100 mL of dimethylformamide under nitrogen is added 3.9 mL (23.6 mmol) of isobutyric anhydride. The reaction mixture is stirred at 50° C. for 1 hour. The solvent is evaporated by Kugelrohr distillation (60° C., 0.01 torr) and the residue is triturated with hot methanol. The remaining solid is recrystallized from methanol:ethyl ether to afford the title compound.

NMR (DMSO-d$_6$): δ=1.00(d,6), 1.13(t,3), 2.32(s,3), 2.39(q,2), 3.77(sept,1), 6.96(d,1), 7.38(d,1), 7.55(m,2), 7.81(m,2) and 11.4(brs,1) ppm.

EXAMPLE VI (1)

4-Ethyl-1,3-dihydro-5-[4-(2-methyl-1H-imidazol-1-yl)benzoyl]-1,3-bis[1-oxo-2-phenylethyl]-2H-imidazol-2-one.

and

(2)

4-Ethyl-1,3-dihydro-5-[4-(2-methyl-1H-imidazol-1-yl)benzoyl]-1-(1-oxo-2-phenylethyl)-2H-imidazol-2-one.

To a suspension of 4.2 g (13.2 mmol) of the product of Example I in 35 mL of dimethylformamide is added 3.1 g (19.3 mmol) of phenylacetylchloride in a dropwise fashion. The resulting mixture is stirred at 65° C. under nitrogen for 40 hours. The reaction mixture is cooled and filtered. The filtrate is diluted with 200 ml of ethyl ether and the resulting precipitate is subjected to flash chromatography on silica gel utilizing 5% methanol in methylene chloride as the eluent. The eluates are analyzed utilizing thin layer chromatography and appropriate fractions are combined and evaporated to produce the above referenced products (1) and (2).

We claim:

1. A compound of the formula:

wherein

R is H or $R_1$ is phenyl or a $C_1$–$C_5$ straight or branched chain alkyl optionally substituted by a hydroxy, or phenyl group;

or a pharmaceutically acceptable acid addition salt thereof.

2. A compound of claim 1 wherein R is

3. A compound of claim 2 wherein $R_1$ is phenyl which is 1,3-dibenzoyl-4-ethyl-1,3-dihydro-5-[4-(2-methyl-1H-imidazol-1-yl)benzoyl]-2H-imidazol-2-one.

4. A compound of claim 2 wherein $R_1$ is a $C_1$–$C_5$ straight or branched chain alkyl.

5. A compound of claim 2 wherein $R_1$ is a $C_1$–$C_5$ straight or branched chain alkyl substituted by a phenyl group.

6. A compound of claim 2 wherein $R_1$ is a $C_1$–$C_5$ straight or branched chain alkyl substituted by a hydroxy group.

7. A compound of claim 4 which is 1,3-diacetyl-4-ethyl-1,3-dihydro-5-[4-(2-methyl-1H-imidazol-1-yl)benzoyl]-2H-imidazol-i2-one.

8. A compound of claim 4 which is 4-ethyl-1,3-dihydro-5-[4-(2-methyl-1H-imidazol-1-yl)benzoyl]-1,3-bis[2-methyl-1-oxopropyl]-2H-imidazol-2-one.

9. A compound of claim 4 which is 4-ethyl-1,3-bis-[2-ethyl-1-oxobutyl]-1,3-dihydro-5-[4-(2-methyl-1H-imidazol-1-yl)benzoyl]-2H-imidazol-2-one.

10. A compound of claim 4 which is 4-ethyl-1,3-dihydro-5-[4-(2-methyl-1H-imidazol-1-yl)benzoyl]-1,3-bis[1-oxohexyl]2H-imidazol-2-one.

11. A compound of claim 5 which is 4-ethyl-1,3-dihydro-5-[4-(2-methyl-1H-imidazol-1-yl)benzoyl]-1,3-bis[1-oxo-2-phenylethyl]-2H-imidazol-2-one.

12. A compound of claim 5 which is 4-ethyl-1,3-dihydro-5-[4-(2-methyl)-1H-imidazol-1-yl)benzoyl]-1,3-bis[2-methyl-1-oxo-2-phenyethyl]-2H-imidazol-2-one.

13. A compound of claim 6 which is 4-ethyl-1,3-dihydro-1,3-bis[3-hydroxy-1-oxopropyl]-5-[4-(-2-methyl-1H-imidazol-1-yl)benzoyl]-2H-imidazol-2-one.

14. A compound of claim 6 which is 4-ethyl-1,3-dihydro-1,3-bis[3-hydroxy-1-oxobutyl]-5-[4-(2-methyl-1H-imidazol-1-yl)benzoyl]-2H-imidazol-2-one.

15. A compound of claim 6 which is 4-ethyl-1,3-dihydro-1,3-bis[5-hydroxy-1-oxopentyl]-5-[4-(2-methyl-1H-imidazol-1-yl)benzoyl]-2H-imidazol-2-one.

16. A compound of claim wherein R is hydrogen.

17. A compound of claim 16 wherein $R_1$ is phenyl which is 1-benzoyl-4-ethyl-1,3-dihydro-5-[4-(2-methyl-1H-imidazol-1-yl)benzoyl]-2H-imidazol-2-one.

18. A compound of claim 16 wherein $R_1$ is a $C_1$–$C_5$ straight or branched chain alkyl.

19. A compound of claim 18 which is 1-acetyl-4-ethyl-1,3-dihydro-5-[4-(2-methyl-1H-imidazol-1-yl)benzoyl]-2H-imidazol-2-one.

20. A compound of claim 18 which is 4-ethyl-1,3-dihydro-5-[4-(2-methyl-1H-imidazol-1-yl)benzoyl]-1-(2-methyl-1oxopropyl)-2H-imidazol-2-one.

21. A compound of claim 18 which is 4-ethyl-1-[2-ethyl-1-oxobutyl]-1,3-dihydro-5-[4-(2-methyl-1H-imidazol-1-yl)benzoyl]-imidazol-2H-imidazol-2-one.

22. A compound of claim 18 which is 4-ethyl-1,3-dihydro-5-[4-(2-methyl-1H-imidazol-1-yl)benzoyl]-1-(1-oxohexyl)-2H-imidazol-2-one.

23. A compound of claim 16 wherein $R_1$ is a $C_1$–$C_5$ straight or branched chain alkyl substituted by a phenyl group.

24. A compound of claim 23 which is 4-ethyl-1,3-dihydro-5-[4- (2-methyl-1H-imidazol-1-yl)benzoyl]-1-(1-oxo-2-phenylethyl)-2H-imidazol-2-one.

25. A compound of claim 23 which is 4-ethyl-1,3-dihydro-5-[4-(2-methyl-1H-imidazol-1-yl)benzoyl]-1-(2-methyl-1-oxo-2-phenylethyl)-2H-imidazol-2-one.

26. A compound of claim 16 wherein $R_1$ is a $C_1$–$C_5$ straight or branched chain alkyl substituted by a hydroxy group.

27. A compound of claim 26 which is 4-ethyl-1,3-dihydro-1-[3-hydroxy-1-oxopropyl]-5-[4-(2-methyl-1H-imidazol-1-yl)benzoyl]-2H-imidazol-2-one.

28. A compound of claim 26 which is 4-ethyl-1,3-dihydro-1-[3-hydroxy-1-oxobutyl]-5-[4-(2-methyl-1H-imidazol-1-yl)benzoyl]-2H-imidazol-2-one.

29. A compound of claim 26 which is 4-ethyl-1,3-dihydro-1-[5-hydroxy-1-oxopentyl]-5-[4-(2-methyl-1H-imidazol-1-yl)benzoyl]-2H-imidazol-2-one.

30. The method for orally treating cardiac failure in a mammalian host having a chronic condition in which therapeutic benefit is derived from elicitation of a cardiotonic effect which comprises orally administering to said host a non-toxic cardiotonically effective amount of a compound of claim 1.

31. A pharmaceutical composition for oral use in the treatment of cardiac failure comprising a non-toxic cardiotonically effective amount of a compound of claim 1 in admixture with a non-toxic pharmaceutically acceptable carrier.

* * * * *

UNITED STATES PATENT AND TRADEMARK OFFICE
CERTIFICATE OF CORRECTION

PATENT NO. : 4,743,612

DATED : May 10, 1988

INVENTOR(S) : Paul W. Erhardt, Alfred A. Hagedorn, III

It is certified that error appears in the above-identified patent and that said Letters Patent is hereby corrected as shown below:

Column 1, line 28 "imidazolyl-2-one, that is" should read .... imidazol-2-one, that is ....

Column 1, line 35 "at least bioavailable" should read .... at least 75% bioavailable ....

Column 2, line 66 "imidazol-i2-one" should read .... imidazol-2-one ....

Column 5, line 39 "with mixtures of III and !I," should read .... with mixtures of III and II ....

Column 8, line 33 "imidazol-1-yl)benzoyl]2H-imidazol-2-one" to read -- imidazol-1-yl)benzoly]-2H-imidazol-2-one --.

Column 8, line 41 "distillation in vacuo ($\leq$ 55°C)." should read .... distillation in vacuo ($\leq$ 55°C). ....

Column 10, line 52 "imidazol-i2-one" should read .... imidazol-2-one ....

Column 11, line 10 "A compound of Claim wherein R is hydrogen" should read .... A compound of Claim 1 wherein R is hydrogen ....

UNITED STATES PATENT AND TRADEMARK OFFICE
CERTIFICATE OF CORRECTION

PATENT NO. : 4,743,612

DATED : May 10, 1988

INVENTOR(S) : Paul W. Erhardt, Alfred A. Hagedorn, III

It is certified that error appears in the above-identified patent and that said Letters Patent is hereby corrected as shown below:

Column 11, line 21 "(2-methyl-1oxopropyl)" should read .... (2-methyl-1-oxopropyl) ....

Signed and Sealed this

Thirtieth Day of May, 1989

Attest:

DONALD J. QUIGG

Attesting Officer

Commissioner of Patents and Trademarks